United States Patent [19]
Formica et al.

[11] Patent Number: 5,551,310
[45] Date of Patent: Sep. 3, 1996

[54] DETECTION DEVICE WITH A GAS DETECTOR ELEMENT

[75] Inventors: Philip M. Formica, Lübeck; Wolfgang May, Reinfeld; Lore Evers, Lübeck, all of Germany

[73] Assignee: Drägerwerk AG, Lubeck, Germany

[21] Appl. No.: 515,811

[22] Filed: Aug. 16, 1995

[30] Foreign Application Priority Data

Sep. 10, 1994 [DE] Germany ............... 44 32 218.6

[51] Int. Cl.⁶ ........................................... G01N 1/22
[52] U.S. Cl. ...................... 73/863.86; 73/863.01; 73/863.81
[58] Field of Search ............... 73/863.01, 863.02, 73/863.21, 863.81, 863.83, 863.85, 863.86, 864.73, 864.81; 422/85–87

[56] References Cited

U.S. PATENT DOCUMENTS 3,764,270  10/1973  Collier et al. ............... 73/863.02
4,300,384  11/1981  Wiegner et al. ............. 73/863.01
4,598,581  7/1986   Brekke ....................... 73/117.3
4,923,806  5/1990   Klodowski .................. 422/86
5,139,746  8/1992   Rabenecker ................ 422/86
5,321,972  6/1994   Stock ......................... 73/863.02

FOREIGN PATENT DOCUMENTS 1093113  11/1955  Germany.
2731361  7/1977   Germany.

Primary Examiner—Robert Raevis
Attorney, Agent, or Firm—McGlew and Tuttle, P.C.

[57] ABSTRACT

A detection device with a gas detector element for analyzing pressurized gases contained in a reservoir by sampling while the pressure is reduced. A coupling means is provided for connecting the detector to a reservoir. Ease of handling is facilitated in the routine operation by providing a timekeeping device determining the duration of the sampling flow set at a preselected value. A switch starts the timekeeping device, and the switch is actuated at least at the time of the coupling of the detector to the reservoir.

22 Claims, 2 Drawing Sheets

DETECTION DEVICE WITH A GAS DETECTOR ELEMENT

FIELD OF THE INVENTION

The present invention pertains to a detection device with a gas detector element for analyzing pressurized gases contained in a reservoir by sampling while reducing the pressure and with a coupling means for connecting the detection device to the reservoir.

BACKGROUND OF THE INVENTION

A detection device of the above-described type has become known from DE-C 27 31 361. The detection device is connected to a pressurized gas container or a pressurized gas line via a coupling. Besides the coupling, it contains a pressure reducer, a shut-off valve interrupting the sampling flow, a flow meter for measuring the sampling flow, and a gas detector tube arranged downstream of the flow meter. To carry out a gas analysis, a predetermined gas sample volume is passed through the gas detector tube, and the percentage of the component to be detected in the pressurized gas is determined on the basis of the change in the color of the reaction layer of the gas detector tube.

The disadvantage of the prior-art device is that a separate time-keeping device, which is often not at hand in routine operation, is necessary to set the volume of the gas sample. Since the user also must manually determine the gas sampling interval with the time-keeping device, deviations in the gas sample volume to be set from the actually occurring gas sample volume cannot be ruled out, and the concentration value read on the gas detector tube will be inaccurate.

A device for measuring certain components in air or other gases has become known from DE-PS 10 93 113, in which individual detector tubes are exposed to a predetermined gas sample volume by means of a control ensured by a timer by the detector tubes being connected to the gas sampling flow by a rack-and-pinion gear controlled by the timer. The prior-art device is designed for the long-term monitoring of gas concentrations, e.g., in work rooms, without an operator having to be involved in the measurement.

SUMMARY AND OBJECTS OF THE INVENTION

The primary object of the present invention is to improve a detection device of the above-described type in terms of its ease of handling in routine operation.

To attain this object, the detection device has a time-keeping device determining a sampling flow set to a preselected value with a switch that starts and/or stops the time-keeping device, and the switch is actuated at least at the time of the coupling of the detection device to the reservoir.

The advantage of the present invention is essentially that the detection device is provided with a time-keeping device, which is activated when the detection device is connected to the reservoir. The starting point of the time-keeping is thus synchronous with the beginning of the sampling. The time-keeping device consists of a clock and a control logic unit, wherein the control logic unit is connected to the switch and starts or stops the clock, depending on the switching position of the switch. By setting the sampling flow to a preselected value and determining the sampling time by the time-keeping device, the measurement process can be extensively automated. The switch activating the time-keeping device is activated at least at the time of the coupling of the detection device to the reservoir. The clock is advantageously automatically stopped by means of the switch at the time of uncoupling of the detection device from the reservoir.

The switch is preferably arranged in the range of engagement of the coupling means consisting of a coupler plug and a coupling sleeve.

A shut-off element located between the coupling means and the gas detector element is advantageously actuated by the switch or the time-keeping device. The sampling flow is thus released only when the time-keeping device is activated.

The shut-off element is preferably switched into the closed position by the switch and/or the time-keeping device after the end of the preselected measurement time. Thus, e.g., a fixed measurement time, after the end of which the shut-off valve is closed and the clock is stopped at the same time, may be programmed in the control logic unit.

A plurality of gas detector tubes connected in parallel in terms of flow are preferably provided as gas detector elements.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which a preferred embodiment of the invention is illustrated.

DESCRIPTION OF THE PREFERRED EMBODIMENT

Figure 1:
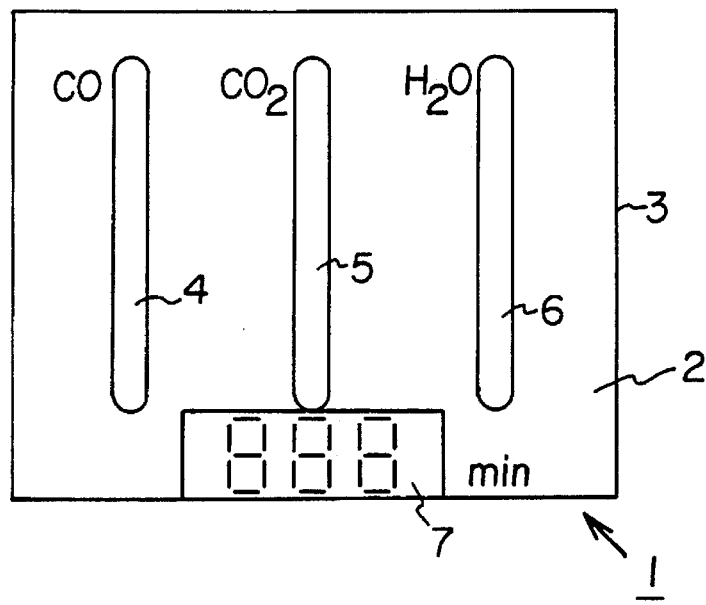
FIG. 1 is a top view of a detection device.

A first gas detector tube 4 for detecting CO, a second gas detector tube 5 for detecting $CO_2$, and a third gas detector tube 6 for detecting $H_2O$ vapor, and a display unit 7 of a time-keeping device, not shown in FIG. 1, are arranged behind a front plate 2 of a housing 3 in the detection device shown in FIG. 1.

Figure 2:
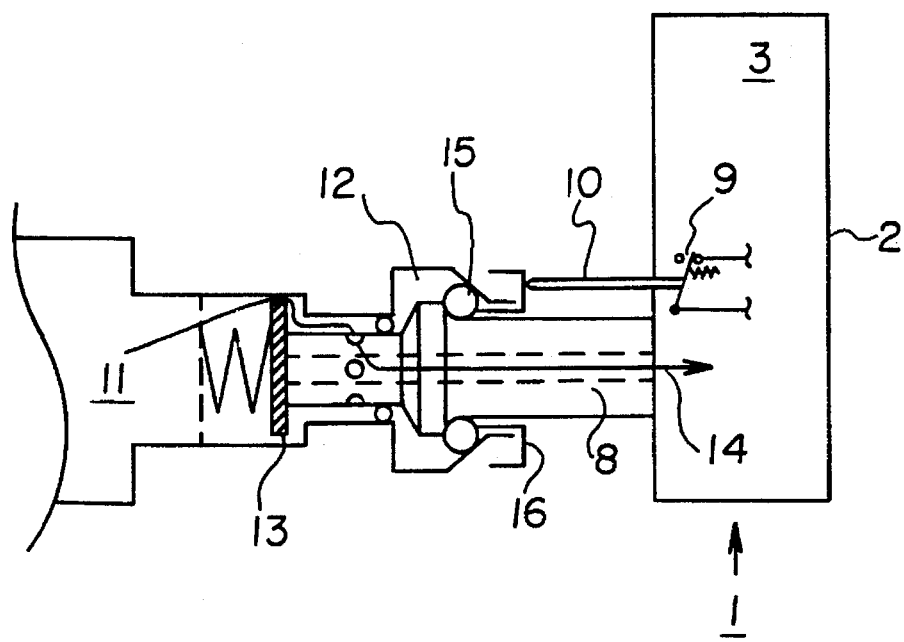
FIG. 2 is a side view of the detection device according to FIG. 1.

As is illustrated in FIG. 2, a coupler plug 8 and a switch 9 with an actuating pin 10 are fastened on the side of the housing 3 located opposite the front side 2, wherein the switch 9 engages, via the actuating pin (contact portion) 10, a coupling sleeve 12, into which the coupler plug 8 is inserted. The coupling sleeve 12 is connected to a reservoir 11 filled with pressurized gas, which is shown only partially in FIG. 2. A nonreturn valve 13, which interrupts the gas flow from the reservoir 11 when the coupler plug 8 is pulled out, is located within the coupling sleeve 12. The gas flow from the reservoir 11 into the detection device 1 is illustrated by an arrow 14. The coupler plug 8 is locked inside the coupling sleeve 12 with a detachable locking means 15, which releases the coupler plug 8 upon pressure on a ring 16.

Figure 3:
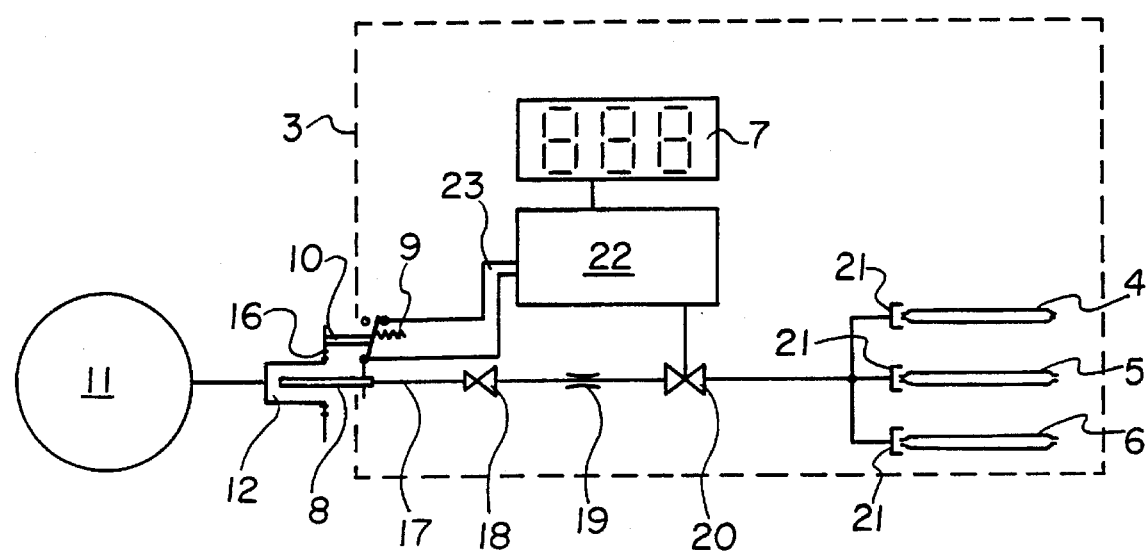
FIG. 3 is a pneumatic circuit diagram of the detection device.

FIG. 3 schematically shows the pneumatic circuit diagram of the detection device 1. Identical components are designated by the same reference numbers as in FIGS. 1 and 2. A pressure reducer 18, a fixed throttle 19 for setting a preselected sampling flow, a shut-off valve 20, and analysis connections 21 for connecting the gas detector tubes 4, 5, 6 are arranged in the line 17 originating from the coupler plug 8. A time-keeping device 22 is connected to connection lines 23 of the switch 9, to the shut-off valve 20 and to the display unit 7. The mode of operation of the detection device 1 according to the present invention is as follows: When the coupler plug 8 is plugged into the coupling sleeve 12, the actuating pin 10 touches the ring 16, and the switch 9 switches over into the closed position. A control logic unit, which is not shown in FIG. 3 and opens the shut-off valve 20 and starts the clock of the time-keeping device, is located within the time-keeping device 22. The measurement time can be read in minutes on the display unit 7. With the shut-off valve 20 opened, the sampling flow limited by the fixed throttle 19 flows through the gas detector tubes 4, 5, 6. After the end of the measurement time, which is normally a few minutes, the coupler plug 8 is pulled out of the coupling sleeve 12, the actuating pin 10 now becomes disengaged from the ring 16, and the switch 9 switches over into the open position. The clock is stopped and the shut-off valve 20 is closed by the control logic unit of the time-keeping device 22. The concentrations of the components to be detected in the gas sample can be read on the gas detector tubes 4, 5, 6 on the basis of the changes in the color of the reaction zones of the gas detector tubes.

While a specific embodiment of the invention has been shown and described in detail to illustrate the application of the principles of the invention, it will be understood that the invention may be embodied otherwise without departing from such principles.

What is claimed is:

1. A detection device, comprising:

a detector means for analyzing pressurized gases;

a reservoir containing pressurized gas to be analyzed;

coupling means for connecting said detector means to said reservoir for providing a sampling flow from said reservoir to said detector means, said detector means including timing means for determining a duration of a sampling flow; and switching means connected to said timing means for starting and/or stopping said timing means, said switching means being actuated upon coupling and/or decoupling said detector means to/from said reservoir.

2. A detection device according to claim 1, wherein said switching means includes a contact portion for engagement with said coupling means, said coupling means including a coupler plug and a coupling sleeve.

3. A detection device according to claim 1, wherein said detector means includes a gas detector element and shut-off means provided in a line section between said gas detector element and said coupling means.

4. A detection device according to claim 3, wherein said shut-off means is connected to one of said timing means and said switching means, said shut-off means being switched into a closed position by said one of said timing means and said switching means.

5. A detection device according to claim 4, wherein said shut-off means includes an shut-off element switchable between a closed position and an open position, said shut-off means being connected to said timing means, said shut-off element being switched into a closed position after a predetermined measurement time.

6. A detection device according to claim 1, wherein said detector means includes a gas detector element with a plurality of gas detector tubes, through which gas flows in parallel.

7. A detection device according to claim 1, wherein said detector further includes analysis connections with connected gas detector tubes and flow setting means for setting a predetermined sampling flow, said flow setting means being disposed upstream of said analysis connections.

8. A detection device according to claim 7, wherein said flow setting means comprises a pressure reducer and a fixed throttle, said fixed throttle being connected between said pressure reducer and said analysis connections.

9. A detection device, comprising:

detector means for analyzing pressurized gases;

a reservoir containing pressurized gas to be analyzed;

coupling means for connecting said detector means to said reservoir for providing a sampling flow from said reservoir to said detector means, said detector means including timing means for determining a duration of a sampling flow; and switching means connected to said timing means for starting said timing means upon coupling said detector means to said reservoir and for stopping said timing means upon decoupling said detector from said reservoir.

10. A detection device according to claim 9, wherein said switching means includes a contact portion for engagement with said coupling means, said coupling means including a coupler plug and a coupling sleeve.

11. A detection device according to claim 9, wherein said detector means includes a gas detector element and shut-off means provided in a line section between said gas detector element and said coupling means.

12. A detection device according to claim 11, wherein said shut-off means is connected to one of said timing means and said switching means, said shut-off means being switched into a closed position by said one of said timing means and said switching means.

13. A detection device according to claim 9, wherein said detector means includes a gas detector element with a plurality of gas detector tubes, through which gas flows in parallel.

14. A detection device according to claim 9, wherein said shut-off means includes a shut-off element switchable between a closed position and an open position, said shut-off means being connected to said timing means, said shut-off element being switched into a closed position after a predetermined measurement time.

15. A detection device according to claim 9, wherein said detector further includes analysis connections with connected gas detector tubes and flow setting means for setting a predetermined sampling flow, said setting means being disposed upstream of said analysis connections.

16. A detection device according to claim 15, wherein said flow setting means comprises a pressure reducer and a fixed throttle, said fixed throttle being connected between said pressure reducer and said analysis connections.

17. A detection device, comprising:

detector means for analyzing pressurized gases;

a reservoir containing pressurized gas to be analyzed;

coupling means for connecting said detector means to said reservoir for providing a sampling flow from said reservoir to said detector means, said detector means including timing means for timing a duration of a sampling flow; and switching means connected to said timing means, said switching means including a contact portion for detecting engagement of said reservoir with said coupling means, said switching means for actuating said timing means upon connection of said detector means to said reservoir.

18. A detection device according to claim 17, wherein said detector further includes analysis connections with connected gas detector tubes and flow setting means for setting a predetermined sampling flow, said setting means being disposed upstream of said analysis connections.

19. A detection device according to claim 18, wherein said flow setting means comprises a pressure reducer and a fixed throttle, said fixed throttle being connected between said pressure reducer and said analysis connections.

20. A detection device, comprising:

a detector means for analyzing pressurized gases;

a reservoir containing pressurized gas to be analyzed;

coupling means for connecting said detector means to said reservoir for providing a sampling flow from said reservoir to said detector means, said detector means including timing means for determining a duration of a sampling flow; and switching means connected to said timing means for starting said timing means, said switching means includes a contact portion for engagement with said coupling means, said switching means being actuated upon coupling said detector means to said reservoir.

21. A detection device according to claim 20, wherein said detector means includes a gas detector element and shut-off means provided in a line section between said gas detector element and said coupling means.

22. A detection device according to claim 20, further comprising shut-off means connected to said timing means and said switching means, said shut-off means being switched into a closed position by said timing means.

* * * * *